United States Patent [19]

Sitte

[11] Patent Number: 4,489,569

[45] Date of Patent: Dec. 25, 1984

[54] COOLING APPARATUS FOR THE RAPID COOLING OF SPECIMENS

[75] Inventor: Helmuth Sitte, Seefeld, Austria

[73] Assignee: C. Reichert Optische Werke AG., Vienna, Austria

[21] Appl. No.: 532,943

[22] Filed: Sep. 16, 1983

[30] Foreign Application Priority Data

Sep. 17, 1982 [DE] Fed. Rep. of Germany ....... 3234457

[51] Int. Cl.$^3$ .............................................. F25B 19/00
[52] U.S. Cl. ..................... 62/514 R; 62/49; 62/55
[58] Field of Search ................... 62/45, 49, 78, 514 R, 62/55

[56] References Cited

U.S. PATENT DOCUMENTS

| | | | |
|---|---|---|---|
| 3,066,222 | 11/1962 | Poorman et al. | 62/514 R |
| 3,110,157 | 11/1963 | Radd | 62/49 |
| 3,880,193 | 4/1975 | Lewis | 62/55 |
| 4,327,799 | 5/1982 | Scheiwe et al. | 62/78 |
| 4,336,691 | 6/1982 | Burstein et al. | 62/78 |

Primary Examiner—Ronald C. Capossela
Attorney, Agent, or Firm—Alan H. Spencer; Stephen Raines

[57] ABSTRACT

A cooling apparatus utilizing liquid nitrogen for cooling specimens to temperatures in the range from −100° C. to −195° C. in propane, halogenated hydrocarbons, isopentane, or other cooling media. Freezing of the cooling media is avoided by means of an arrangement wherein the liquid nitrogen cools the cooling-bath container and/or the liquifier only initially, but after the desired cooling-bath temperature has been reached, the liquid nitrogen level is lowered to below the height of a protective shell which results in further cooling being only indirect, via solid/solid contacts and via the gas phase. A constant cooling-bath temperature is ensured by means of a thermostatic temperature-control system while trouble-free standby operation is ensured by means of an automatic system for replenishing liquid nitrogen, and by a system for controlling the level of liquid nitrogen. Safe disposal of the cooling media which may be combustible and/or toxic is provided for.

12 Claims, 7 Drawing Figures

COOLING APPARATUS FOR THE RAPID COOLING OF SPECIMENS

BACKGROUND OF THE INVENTION

The invention relates to a cooling apparatus for the rapid cooling of specimens to cryogenic temperatures, in particular for the cryofixation of biological specimens for subsequent optical or electron-optical examination.

PRIOR ART

Cooling baths, with volumes of between 5 and 100 ml, maintained at temperatures in the range from −100° C. to −190° C. are required for numerous sample-preparation operations, in particular, for the instantaneous freezing ("cryofixation") of biological specimens for optical or electron-optical examination. The specimens normally have diameters ranging from 0.5 mm to 5 mm.

The specimens should be rapidly cooled on being introduced into the cooling bath and this can be achieved only when the cooling liquid is prevented from boiling as the specimen is introduced since the formation of a gas blanket ("Leyden-frost phenomenon") around the specimen prevents the rapid heat exchange which is necessary. Liquid nitrogen is unsuitable for use since under normal conditions it is always at its boiling temperature (−196° C.) and, as a result, the slightest heat input gives rise to boiling. Even subcooling the liquid nitrogen down to its freezing point does not improve the situation appreciably due to the small temperature difference between the boiling and freezing points (14° C.) and the fact that both the specific heat and the density of liquid nitrogen are low.

Accordingly, liquified gases which can be cooled well below their boiling points, and which, near their freezing points, exhibit comparatively high densities and specific heats, are generally used for cooling baths. Among others, the following substances exhibit favorable properties: propane (f.p. −190° C.), Freon 13 (f.p. −185° C.), and isopentane (f.p. −160° C.). However, none of these cooling media, which are known and in common use at the present time, exhibits a freezing point which is lower than the boiling point of liquid nitrogen (−196° C.). The cooling of these media, by means of liquid nitrogen, as generally practiced, always requires the application of special skills, since, following the liquefaction or initial cooling, the freezing points of these media are very quickly reached, and a frozen cooling bath can no longer be used. This is particularly troublesome when it is desired to employ cooling baths of this type under continuous-operation conditions, as is the case in the majority of laboratories.

OBJECT OF THE INVENTION

An object of the present invention is to avoid the above-mentioned disadvantages and to provide a cooling bath in which the above-mentioned media (propane, halogenated hydrocarbons such as grades of Freon or Frigen, isopentane, etc.) can be quickly liquified, or initially cooled, by means of liquid nitrogen (liquid nitrogen is both easy to use and hazard-free at all times) and in which cooling bath the medium in question can be kept for extended periods at a temperature which is only slightly above the freezing point of that particular medium, thereby ensuring that the cooling effect is optimum, without the risk of the baths freezing.

BRIEF DESCRIPTION OF THE INVENTION

According to the present invention, we provide a cooling apparatus for the rapid cooling of specimens comprising:

an outer container having an upper rim and adapted to receive a liquid cryogen, an intermediate container, having an upper rim and being arranged inside the outer container, cooling means having an upper rim and being adapted to receive a cooling medium, the cooling means being disposed within said intermediate container, the upper rim of the intermediate container being located below both the upper rim of the outer container and the upper rim of the cooling means, whereby cryogen from the outer container can flow into the intermediate container.

The cooling means may comprise a cooling bath, a liquifier, or both.

The invention thus provides for the liquid nitrogen to come into direct contact with a cooling bath and/or a liquefaction only during the step of liquefaction or of initial cooling. This direct contact can be discontinued, by simple means, at the moment when a preselected temperature is reached, so that, after this temperature has been reached, cooling is effected exlcusively via intermediate elements, and via the gaseous nitrogen phase.

In its simplest form, a system according to the invention can comprise, for example, an arrangement wherein a known type of gas liquifier, and/or cooling bath, is, or are, located in a pot-shaped container being the intermediate container. The upper rim of the pot-shaped container is at a markedly lower level than the upper rim of the cooling bath. The pot-shaped container is disposed within a larger pot being the outer container, the height of which corresponds at least to that of the cooling bath or liquifier. If liquid nitrogen is introduced into the larger pot, the smaller pot fills with liquid nitrogen as soon as the liquid level in the larger pot rises above the height of the rim of the smaller pot. If this occurs, liquid nitrogen comes into direct contact with the liquifier, and/or with the cooling bath, and cools these components extremely rapidly.

Since, during this process, a comparatively large quantity of liquid nitrogen evaporates, it is necessary to replenish the liquid nitrogen at certain time intervals. As long as the cooling bath has still not reached the desired low temperature, replenishment is carried out such that the liquid nitrogen level remains above the rim of the smaller pot, in which situation direct liquid nitrogen cooling is maintained. At the moment when the desired temperature is reached, further replenishing is carried out at a lower level, lying somewhat below the upper rim of the smaller pot.

The liquid nitrogen inside the smaller pot evaporates very rapidly, depending upon the geometrical shape of the pot, after which the liquifier, and/or the cooling bath, continue to be cooled only via the solid/solid contacts, and via the gaseous nitrogen phase, it being relatively simple to dimension the solid/solid contacts so that the heat transfer is that desired for maintaining the cooling temperature.

It is preferred that the larger pot, being the outer container, is thermally insulated, which minimizes the loss of liquid nitrogen. This can be effected either by means of a layer of porous insulation (glass wool, powder, foamed material, or the like), or by means of a design involving an evacuated double shell in the manner of a thermos flask.

A further embodiment of the invention comprises an arrangement wherein the temperature of the liquifier, and/or of the cooling bath, can be measured by means of a temperature sensor, and can be read-off on an indicating instrument. Further embodiments of the invention can involve arrangements whereby the temperature of the above-mentioned elements is kept constant by means of a thermostatically-controlled heating element, and whereby the desired temperature can be preselected by means of a setting element.

The requirement for extended operation in routine service can be met by a further embodiment of the invention in which introduction of the liquid nitrogen by hand is eliminated, together with the need for continuous observation of the liquid nitrogen level in the apparatus. This arrangement involves supplying the liquid nitrogen from a comparatively large stock vessel, and controlling the supply by means of level sensors, it being possible to arrange for at least two different level settings, one for the initial cooling, and one for standby operation once the desired temperature has been reached. This arrangement can be further developed by arranging for the change over from the higher level sensor to the lower level sensor to be initiated automatically on reaching the preselected cryogen temperature.

When combustible or toxic cryogens are used (e.g. propane), problems can arise as a result of the spontaneous evaporation of the cooling medium into the atmosphere. Also, it may be necessary to preserve expensive cooling-bath contents in order to be able to use them again without the continuous consumption of liquid cryogen. To meet these problems a further embodiment of the invention can take the form of an arrangement wherein the cryogen occupies a light-weight insert which can be removed from the complete apparatus in a simple manner. In addition, an embodiment can include an arrangement whereby this insert can be inserted into a pressure vessel which possesses a gas-tight closure, and a valve which is suitable for venting-off the gas, in a metered manner, once its temperature has risen to room temperature. A device of this type enables, on the one hand, the cooling medium to be used again by being reliquified, or on the other hand, it also makes it possible to flare-off a combustible gas slowly by means of a burner (e.g. a propane gas burner) which process permits its safe disposal.

The invention can also be embodied in a manner which facilitates the direct attachment to suitable injectors for introducing the samples into the cooling bath so that both the loading of these devices and the release of the "injection" can be carried out directly on the apparatus in regions which are economically favorable. A further embodiment can take the form of an arrangement wherein several part elements are combined in one workpiece, for example, a casting or molding, in order to simplify the manufacture, and to reduce the production costs.

BRIEF DESCRIPTION OF THE DRAWINGS

Specific embodiments of the invention are described below in more detail with reference to the drawings, in which.

DETAILED DESCRIPTION OF THE INVENTION

Figure 1:
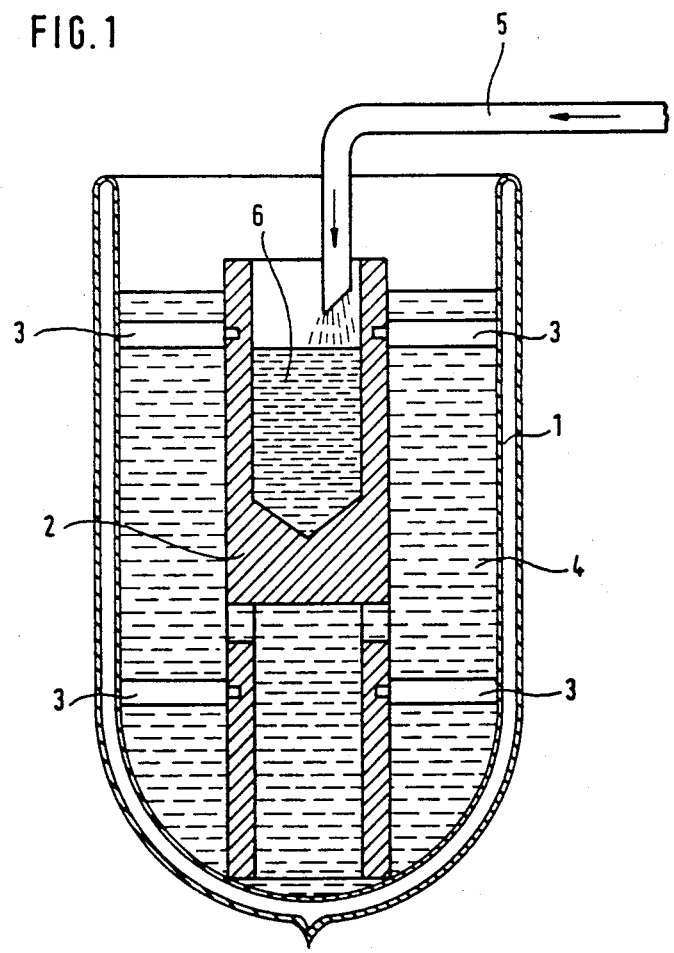
FIG. 1 is a diagrammatic view, in cross-section, of a known type of cooling apparatus cooled by means of liquid nitrogen.

A system corresponding to the present state of the art is shown, in cross-section, in FIG. 1. The cooling bath comprises a cylindrical metal container 2 located in a Dewar vessel 1, the container 2 being spaced from the vessel 1 by spacer elements 3. The Dewar vessel 1 is filled with liquid nitrogen 4. A gas (e.g. propane) can be led through a tube 5, in the direction of the arrows, into the container 2 so that the gas condenses inside the precooled container. The condensate of the liquid, which is led in through the tube 5, serves as the cooling medium 6 in the bath. Alternatively, the cooling medium 6 can be introduced as a liquid.

The disadvantages of cooling baths of this type have already been discussed.

If precautions are taken to avoid freezing of the cooling medium by the liquid nitrogen in such apparatus, by removing the container 2 from the Dewar vessel 1, not only does the cooling bath warm up within an extremely short time but heavy frost formation also occurs on all surfaces of the container 2, as well as on the cooling bath 6, as a result of precipitation of the moisture which is present in the air. Only in the dry nitrogen atmosphere inside the Dewar vessel does this frost formation fail to occur.

Figure 2:
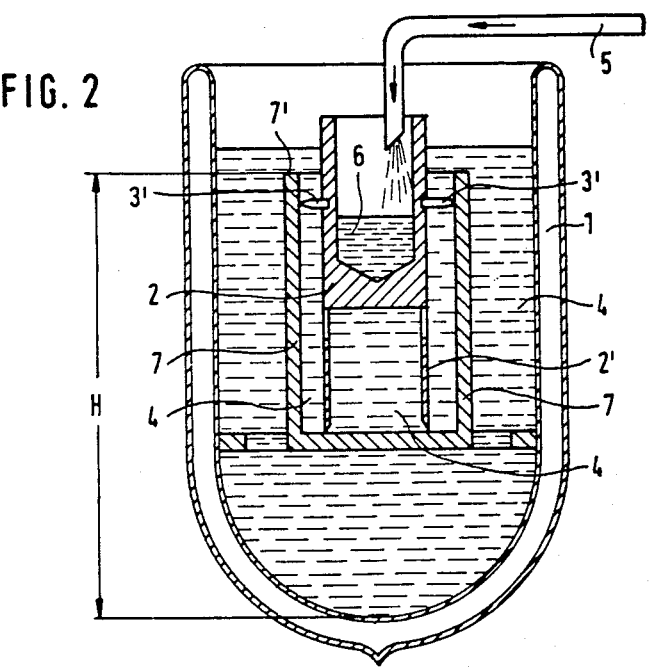
FIGS. 2 and 3 are diagrammatic representations, in cross-section, of a first embodiment of a cooling apparatus with a liquifier, according to the invention, shown in two different operating conditions.
Figure 3:
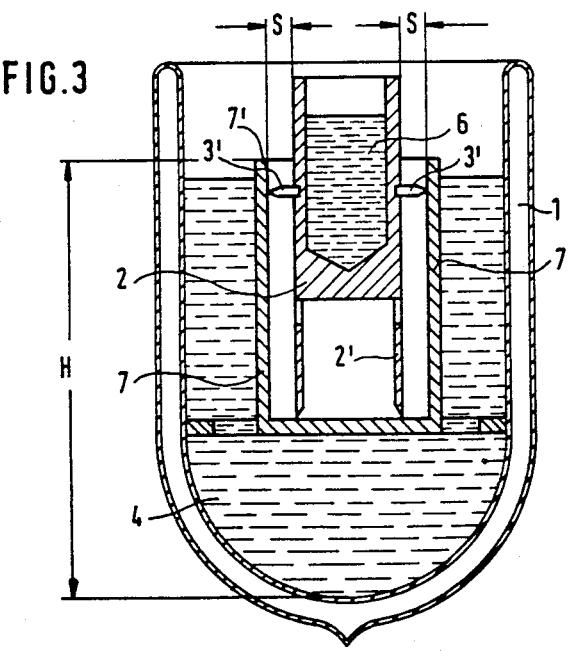

One apparatus, according to the invention, is shown in FIGS. 2 and 3. The container 2 for the cooling medium is not located directly inside the Dewar vessel 1 but is inserted in an intermediate pot 7, which pot may be located in the vessel 2 by means of spacer elements similar to the elements 3 shown in FIG. 1.

The arrangement, during the initial stage of cooling or liquefaction of the gas, is shown in FIG. 2. During this stage, the level of the liquid nitrogen is higher than the height H of the upper rim 7' of the pot 7. Accordingly, liquid nitrogen is in direct contact with all surfaces of the container 2. At this time, the container 2 is still at a temperature considerably above the boiling point of the liquid nitrogen and there is copious boiling-off of the liquid nitrogen. When the container 2 has reached the desired temperature, the replenishment of liquid nitrogen is stopped until its level falls below the upper rim 7' of the pot 7 (height H). Immediately, the comparatively small quantity of liquid nitrogen in the pot 7 evaporates very rapidly so that the stage represented in FIG. 3 is arrived at. At this stage, no part of the container 2 is cooled directly by liquid nitrogen and the cooling takes place via the spacer elements 3' and the hollow cylinder 2'. The amount of such cooling can be determined by the design of the apparatus, e.g. choice of cross-sections and the areas of contact with the pot 7. Some additional cooling is also effected by the cold nitrogen atmosphere which surrounds the container 2.

By designing and dimensioning the elements 3' and 2', and by designing the entire assembly so that it has an appropriate geometrical shape, it is possible to arrange that the temperature of the cooling bath remains slightly above the freezing point of a particular cooling medium. The detailed design of the apparatus, including the gap S between the container 2 and the pot 7, makes it possible to keep the volume of liquid nitrogen inside the pot 7 so small that, once the container 2 has reached the desired temperature, only a very short time is required for the evaporation of the liquid nitrogen from the pot.

However, the assignment of specific dimensions to the components 2, 2', 3' and 7 does not enable the heat transfer between the container 2 and the cooling medium 6, as well as to the surrounding liquid and gaseous nitrogen phases, to be such that all cooling media which could possibly be used (freezing points, for example, between $-190°$ C. and $-150°$ C.) remain in flow-equilibrium states lying slightly above the respective freezing points. As a result, cooling media with comparatively high freezing points will, as a rule, still freeze within a relatively short time.

Figure 4:
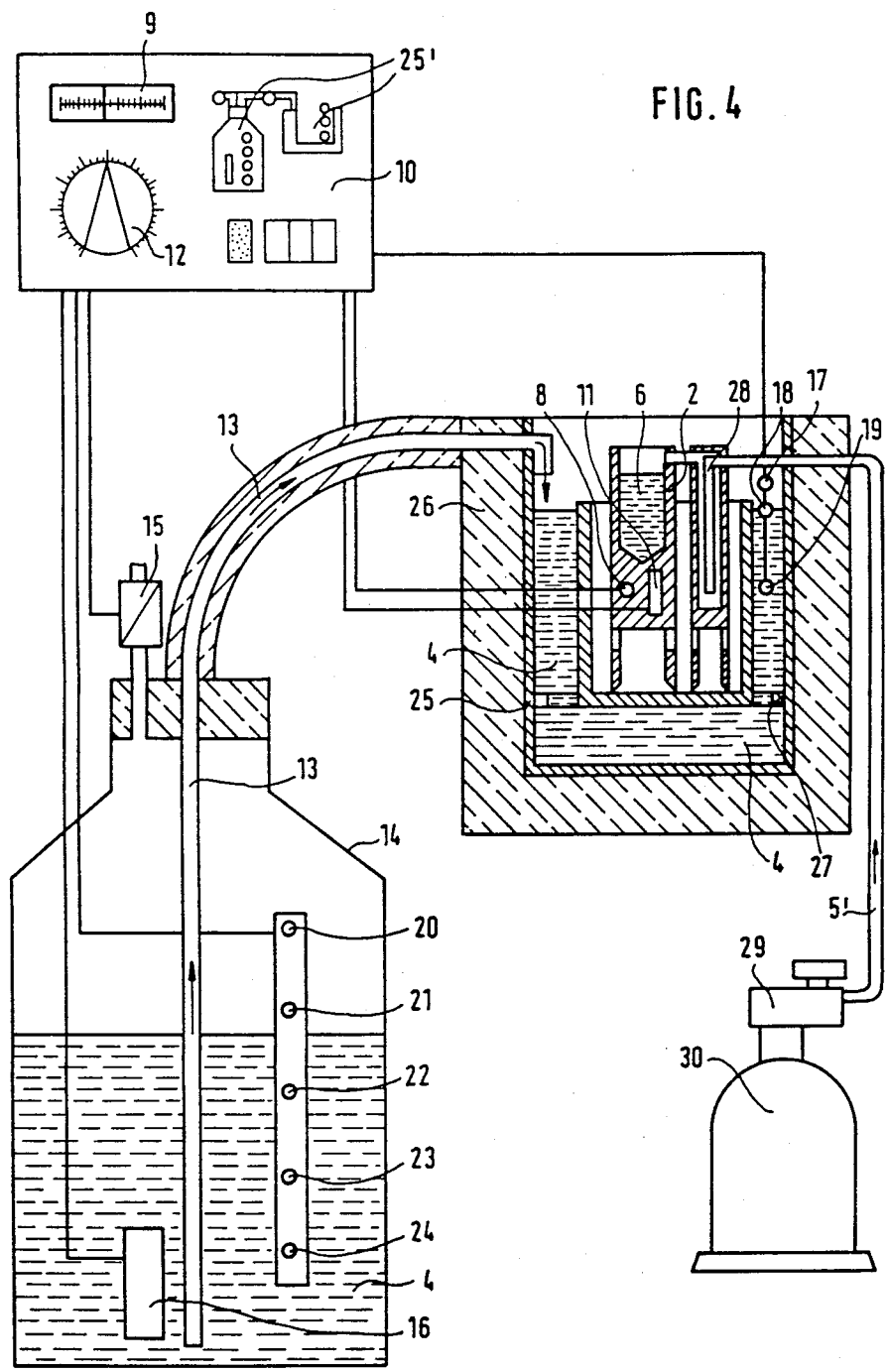
FIG. 4 is a diagrammatic representation of a further embodiment of a cooling apparatus, according to the invention, with a thermostatic-heating system, automatic liquid nitrogen replenishment and level regulation, and a separate liquifier, the latter having an increased output.

This problem is obviated by the further embodiment of the invention, represented in FIG. 4, which employs a temperature sensor 8 in the container 2, which sensor indicates, by means of an indicating instrument 9 on the control unit 10, the temperature reached by the cooling medium 6 at a particular time. As soon as the temperature drops too low, corrective heating can be applied by means of a heating element, for example, a cartridge-type heater 11. One embodiment of the invention uses this heating element 11 in conjunction with the sensor 8 to provide a thermostatic temperature-control system whereby it is possible to preselect a required value. The input to this control system is a setting element, for example, a calibrated rotary knob 12 on the control unit 10.

A further embodiment of the invention involves connecting the assembly to an automatic system for replenishing the liquid nitrogen as shown in FIG. 4. In this case, liquid nitrogen is supplied from an adequately-sized Dewar vessel 14, via a thermally-insulated supply line 13, when the valve 15 is closed and the heating element 16 is switched on.

The elements 15, 16, which are required to obtain the necessary filling pressure, are controlled by means of level sensors 17, 18 and 19 (e.g. heat-sensitive diodes) and the electronic system of the control unit 10. In this process filling initially takes place up to the level which is defined by the diode 17. After the desired temperature has been reached, which is preset by means of the rotary knob 12, the system can be switched over manually, or by automatic means, from the diode 17 to the diode 18. Filling then takes place, in each case, up to the level which is defined by the diode 18.

Where there is a defect in the replenishing system, for example, the consumption of all the liquid nitrogen in the Dewar vessel 14, a further diode 19 can trigger a warning signal when the level of the liquid nitrogen falls below the lower height defined by this diode. The user then has an opportunity to eliminate the fault, for example, to top-up the liquid nitrogen in the Dewar vessel 14.

FIG. 4 also illustrates further developments of the invention. Thus, level sensors (e.g. heat-sensitive diodes 20 to 24) can also be installed in the Dewar vessel 14, these level sensors indicating the contents level by means of an LED display diagram 25' on the control unit 10. As mentioned above, a warning system for the complete consumption of the liquid nitrogen can also be included.

The Dewar vessel 1 may be replaced by, for example, a sheet-metal pot 25 which is surrounded by thermal insulation 26. In this case, the pot 7 can be rigidly mounted on a plate 27 which is connected, in turn, to the pot 25. A liquifier system 28 can be connected via the connection 5', and a reducing valve 29 to a gas bottle 30 (e.g. propane gas).

Figure 5:
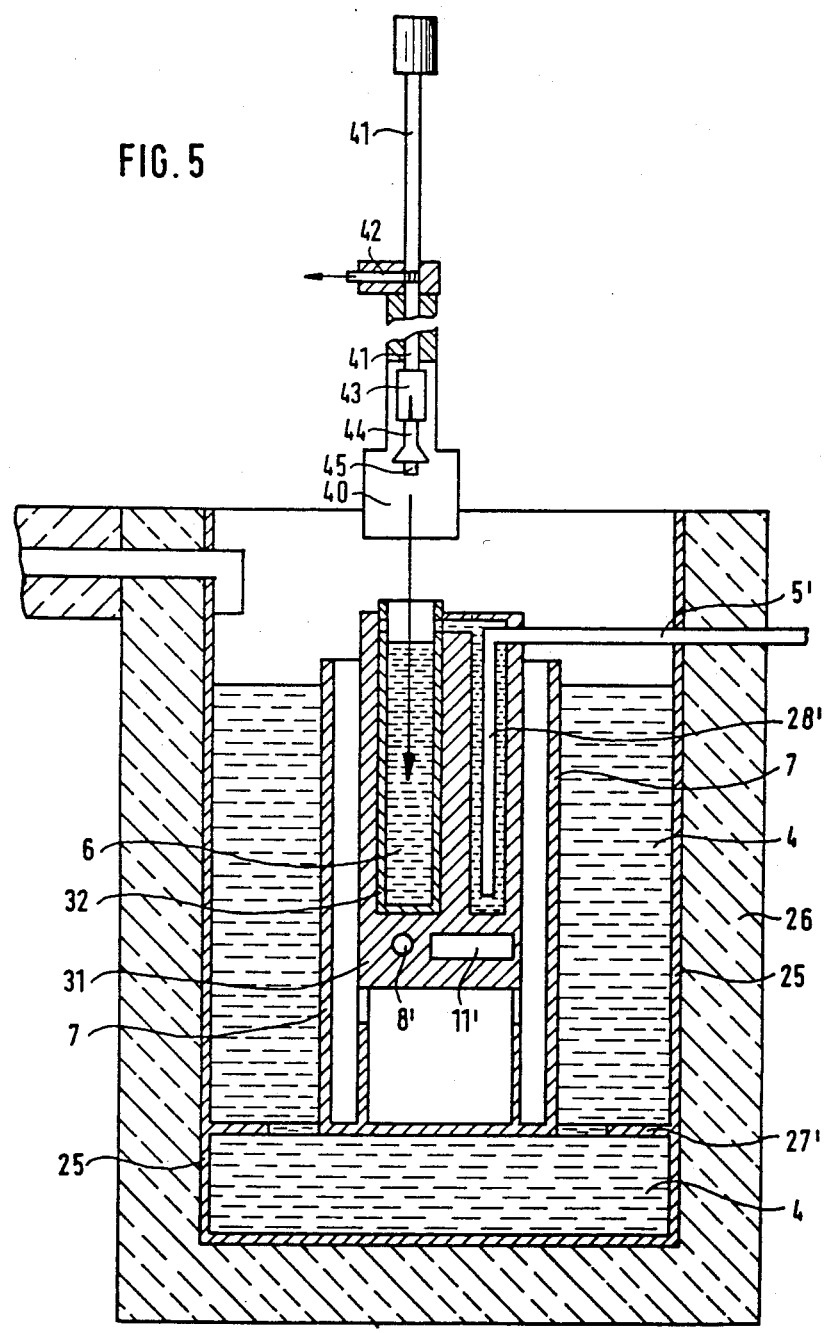
FIG. 5 is a diagrammatic representation of a third embodiment of a cooling apparatus, according to the invention, with a liquifier which is integrated into the apparatus, and with a sample injector attached.

A further variant of the apparatus shown in FIG. 4 is shown in FIG. 5. In this embodiment the gas liquifier 28' is integrated into the cooling bath 31, thus enabling the temperature of the two elements to be measured and controlled jointly by the sensor 8' and the heating element 11' respectively.

FIG. 5 also shows one particular type of injector system as an example of a mechanical connection to the cooling bath, the arrangement comprising an injector holder 40, an injector 41, a release device 42, a mounting element 43, a sample holder 44, and a sample 45.

Figure 6:
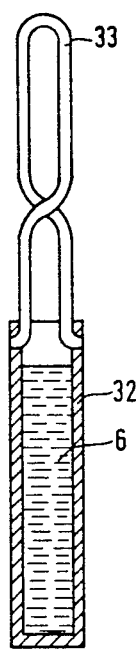
FIG. 6 is a detail representation, in section, of a miniature cooling-medium tube which can be used in conjunction with the third embodiment, shown in FIG. 5.
Figure 7:
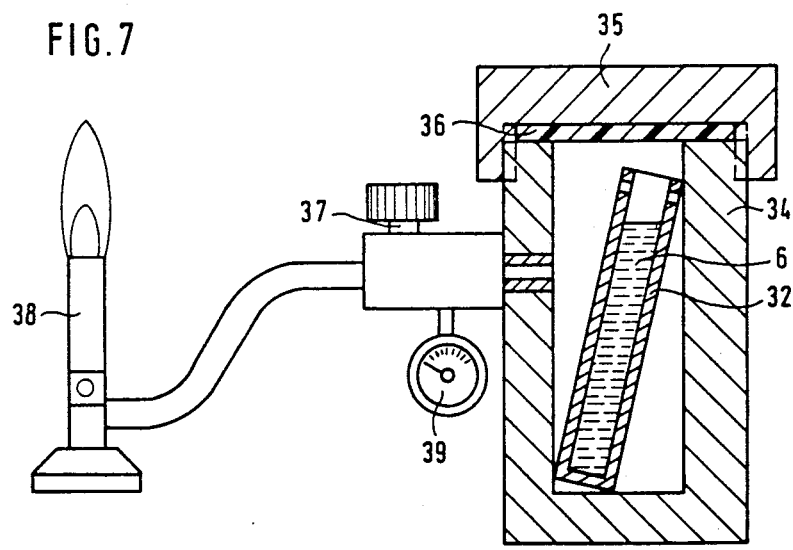
FIG. 7 is a diagrammatic sectional representation of a pressure vessel for the miniature tube shown in FIG. 6, this vessel being connected to a combustion device.

One version of this apparatus takes a form wherein the cooling medium 6 is present in a miniature tube 32 which can be removed from the dual-purpose container 31 by means, for example, of a springy pick-up tool 33 (compare FIG. 6). Since, in many modern laboratory buildings, especially in fully air-conditioned high-rise buildings, there is no facility whereby condensed combustible or toxic gases, such as propane, can be safely evaporated in the open, a further embodiment is shown in FIG. 7. The miniature tube 32 with the cooling medium 6 is inserted in the pressure vessel 34 which is sealed by means of a cover 35 fitted with a sealing ring 36. The cooling medium 6 is then heated to room temperature and the pressure vessel 34 can be emptied via the valve 37. In a closed room, disposal of propane, or of other combustible gases, can be carried out, with safety, by connecting to a burner 38, or the gases can be reliquified and used again by connecting to the liquifier 5', 28'. During these operations the contents level can be monitored by means of a pressure gage 39.

Modifications of the embodiments shown in FIGS. 2 to 7 are possible within the scope of the invention. One possibility is for the apparatus to be manufactured in such a way that several elements are integrated or are connected in a manner different from that represented in the illustrative embodiments. For example, the control unit 10 is represented separately in FIG. 4 but this may be integrated together with the electronic system and all the circuit elements, monitoring elements, and indicating elements to provide a compact arrangement.

Also, the design of the outer container can be varied and different methods of insulation employed. For example, the Dewar vessel 1, or the insulated sheet-metal pot 25, 26, may be replaced by other containers such as evacuated double-shell vessels, made of metal, with or without molecular sieves.

The injection system shown in FIG. 5 can also be replaced by another known type of injection system, and the nitrogen temperature-control arrangements, the replenishment of liquid nitrogen, means for liquifying or cooling, and the monitoring and control systems can all be modified to suit the requirements of a particular apparatus.

I claim:

1. Liquid cooling apparatus having an intermediate vessel capable of transferring heat at two different rates which comprises, a first vessel having an upper rim and being adapted to receive a liquid cryogen, a second vessel having an upper rim supported in said first vessel, the upper rim of said second vessel being located below the upper rim of said first vessel, said second vessel further being adapted to receive liquid cryogen from said first vessel, when the liquid cryogen level is higher than the upper rim of said second vessel, and a third vessel having an upper rim, support means positioning said third vessel in said second vessel with the upper rim of said third vessel being located between the upper rims of said first and second vessels, said third vessel being adapted to receive the liquid to be cooled, whereby the liquid is cooled by rapid heat transfer from the liquid to the liquid cryogen in said second vessel, when said liquid cryogen level in said first vessel is above the upper rim of said second vessel, and maintained at a chosen temperature by slower heat transfer, when said liquid cryogen level in said first vessel is below the upper rim of said second vessel.

2. Apparatus according to claim 1 provided with a sensor for detecting the temperature of said third vessel and means for indicating that temperature.

3. Apparatus according to claim 2 further including a thermostatically-controllable heating element effective to warm said third vessel.

4. Apparatus according to claim 1 further including a reservoir for liquid cryogen operatively connected to said first container and sensing means to control the flow of liquid cryogen to said first vessel.

5. Apparatus according to claim 4, in which said level sensing means concludes a first level sensor adapted to keep the liquid cryogen at a first level in said first vessel, said first level being above the rim of said vessel, and a second level sensor adapted to keep the cryogen at a second level in said first vessel, said second level being below the rim of said second vessel.

6. Apparatus according to claim 1 further including thermostatic switch means for selectively operating one of said first and second level sensors.

7. Apparatus according to claim 1 in which said third vessel is detachable.

8. Apparatus according to claim 7 further including disposal means for burning a combustible cooling liquid.

9. Apparatus according to claim 8 wherein said disposal means includes a container for receiving said third vessel, a burner and a valve connecting said container to said burner, whereby the cooling liquid is burned after warming to room temperature.

10. Apparatus according to claim 1 further including injector means mountains above said third vessel four rapidly immersing specimens into the cool liquid.

11. Apparatus according to claim 1 in which said first vessel is thermally-insulated.

12. Apparatus according to claim 11 in which said first vessel has an evacuated double wall.

* * * * *